(12) United States Patent
Morero et al.

(10) Patent No.: US 8,612,022 B1
(45) Date of Patent: Dec. 17, 2013

(54) NEUROMODULATION CATHETERS AND ASSOCIATED SYSTEMS AND METHODS

(75) Inventors: Massimo Morero, Roncadelle (IT); Carlo Guala, Roncadelle (IT)

(73) Assignee: Invatec S.p.A., Roncadelle (BS) (IT)

( * ) Notice: Subject to any disclaimer, the term of this patent is extended or adjusted under 35 U.S.C. 154(b) by 0 days.

(21) Appl. No.: 13/613,091

(22) Filed: Sep. 13, 2012

(51) Int. Cl.
*A61N 1/00* (2006.01)

(52) U.S. Cl.
USPC .......................................................... 607/116

(58) Field of Classification Search
USPC ............................................ 607/116, 44, 72
See application file for complete search history.

(56) References Cited

U.S. PATENT DOCUMENTS

| | | |
|---|---|---|
| 4,602,624 A | 7/1986 | Naples et al. |
| 4,649,936 A | 3/1987 | Ungar et al. |
| 4,764,504 A | 8/1988 | Johnson et al. |
| 4,976,711 A | 12/1990 | Parins et al. |
| 5,300,068 A | 4/1994 | Rosar et al. |
| 5,345,936 A | 9/1994 | Pomeranz et al. |
| 5,358,514 A | 10/1994 | Schulman et al. |
| 5,368,591 A | 11/1994 | Lennox et al. |
| 5,423,744 A | 6/1995 | Gencheff et al. |
| 5,465,717 A | 11/1995 | Imran et al. |
| 5,476,495 A | 12/1995 | Kordis et al. |
| 5,484,400 A | 1/1996 | Edwards et al. |
| 5,571,147 A | 11/1996 | Sluijter et al. |
| 5,599,345 A | 2/1997 | Edwards et al. |
| 5,626,576 A | 5/1997 | Janssen |
| 5,636,634 A | 6/1997 | Kordis et al. |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,722,401 A | 3/1998 | Pietroski et al. |
| 5,772,590 A | 6/1998 | Webster, Jr. |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |

(Continued)

FOREIGN PATENT DOCUMENTS

| | | |
|---|---|---|
| CN | 2855350 | 1/2007 |
| CN | 102274074 | 12/2011 |

(Continued)

OTHER PUBLICATIONS

U.S. Appl. No. 95/002,110, filed Aug. 29, 2012, Demarais et al.

(Continued)

*Primary Examiner* — Robert N Wieland

(57) ABSTRACT

Catheters, systems, and methods for achieving renal neuromodulation by intravascular access. A catheter has an energy delivery device positionable in a renal blood vessel and being transformable between a radially constrained low-profile state and a self-expanded deployed state. The energy delivery device includes a first electrode array spaced longitudinally from and flexibly connected to a second electrode array, the arrays being sized and shaped so that the electrode regions contact an interior wall of the renal blood vessel when the energy delivery device is in the deployed state. The electrode regions are configured for direct and/or indirect application of thermal and/or electrical energy to heat or otherwise electrically modulate neural fibers that contribute to renal function or of vascular structures that feed or perfuse the neural fibers.

17 Claims, 12 Drawing Sheets

(56) References Cited

U.S. PATENT DOCUMENTS

| | | |
|---|---|---|
| 6,009,877 A | 1/2000 | Edwards |
| 6,066,134 A | 5/2000 | Eggers et al. |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,500,174 B1 | 12/2002 | Maguire et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,692,490 B1 | 2/2004 | Edwards et al. |
| 6,736,835 B2 | 5/2004 | Pellegrino et al. |
| 6,780,183 B2 | 8/2004 | Jimenez, Jr. et al. |
| 6,837,886 B2 | 1/2005 | Collins et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,291,146 B2 | 11/2007 | Steinke et al. |
| 7,381,200 B2 | 6/2008 | Katoh et al. |
| 7,390,894 B2 | 6/2008 | Weinshilboum et al. |
| 7,532,938 B2 | 5/2009 | Machado et al. |
| 7,617,005 B2 | 11/2009 | Demarais et al. |
| 7,647,115 B2 | 1/2010 | Levin et al. |
| 7,653,438 B2 | 1/2010 | Deem et al. |
| 7,678,123 B2 | 3/2010 | Chanduszko |
| 7,717,948 B2 | 5/2010 | Demarais et al. |
| 7,778,703 B2 | 8/2010 | Gross et al. |
| 7,850,685 B2 | 12/2010 | Kunis et al. |
| 8,007,495 B2 | 8/2011 | McDaniel et al. |
| 8,019,435 B2 | 9/2011 | Hastings et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,295,902 B2 | 10/2012 | Salahieh et al. |
| 8,337,492 B2 | 12/2012 | Kunis et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0158584 A1 | 8/2003 | Cates et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0233099 A1 | 12/2003 | Danek et al. |
| 2004/0010289 A1 | 1/2004 | Biggs et al. |
| 2004/0082978 A1 | 4/2004 | Harrison et al. |
| 2004/0215186 A1 | 10/2004 | Cornelius et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2006/0095029 A1 | 5/2006 | Young et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0076409 A1* | 3/2009 | Wu et al. ............... 600/547 |
| 2010/0023088 A1* | 1/2010 | Stack et al. ............ 607/44 |
| 2010/0137860 A1 | 6/2010 | Demarais et al. |
| 2010/0137952 A1 | 6/2010 | Demarais et al. |
| 2010/0168737 A1 | 7/2010 | Grunewald |
| 2010/0191112 A1 | 7/2010 | Demarais et al. |
| 2010/0222851 A1* | 9/2010 | Deem et al. ............ 607/72 |
| 2010/0222854 A1 | 9/2010 | Demarais et al. |
| 2010/0286684 A1 | 11/2010 | Hata et al. |
| 2011/0118726 A1 | 5/2011 | de la Rama et al. |
| 2011/0213231 A1 | 9/2011 | Hall et al. |
| 2011/0257622 A1 | 10/2011 | Salahieh et al. |
| 2011/0301587 A1 | 12/2011 | Deem et al. |
| 2011/0306851 A1 | 12/2011 | Wang |
| 2012/0029500 A1 | 2/2012 | Jenson et al. |
| 2012/0029504 A1 | 2/2012 | Afonso et al. |
| 2012/0029510 A1 | 2/2012 | Haverkost |
| 2012/0071870 A1 | 3/2012 | Salahieh et al. |
| 2012/0130289 A1 | 5/2012 | Demarais et al. |
| 2012/0130345 A1 | 5/2012 | Levin et al. |
| 2012/0157992 A1 | 6/2012 | Smith et al. |
| 2012/0157993 A1 | 6/2012 | Jenson et al. |
| 2012/0172837 A1 | 7/2012 | Demarais et al. |
| 2012/0184952 A1 | 7/2012 | Jenson et al. |
| 2012/0265198 A1 | 10/2012 | Crow et al. |
| 2012/0296232 A1 | 11/2012 | Ng |
| 2012/0296329 A1 | 11/2012 | Ng |
| 2013/0053732 A1 | 2/2013 | Heauser |
| 2013/0090651 A1 | 4/2013 | Smith |
| 2013/0090652 A1 | 4/2013 | Jenson |
| 2013/0096550 A1 | 4/2013 | Hill |
| 2013/0096554 A1 | 4/2013 | Groff et al. |
| 2013/0110106 A1 | 5/2013 | Richarson et al. |
| 2013/0116687 A1 | 5/2013 | Willard |
| 2013/0123778 A1 | 5/2013 | Richardson et al. |
| 2013/0158509 A1 | 6/2013 | Consigny et al. |
| 2013/0158536 A1 | 6/2013 | Bloom |

FOREIGN PATENT DOCUMENTS

| | | |
|---|---|---|
| CN | 202069688 | 12/2011 |
| CN | 202426647 U | 9/2012 |
| CN | 102885648 A | 1/2013 |
| CN | 102885649 A | 1/2013 |
| CN | 102908188 A | 2/2013 |
| CN | 102908189 A | 2/2013 |
| DE | 29909082 | 7/1999 |
| DE | 10252325 | 5/2004 |
| DE | 10257146 | 6/2004 |
| EP | 1009303 B1 | 6/2009 |
| EP | 2429436 | 3/2012 |
| EP | 2498706 | 9/2012 |
| EP | 2519173 | 11/2012 |
| EP | 2558016 | 2/2013 |
| EP | 2598067 | 6/2013 |
| EP | 2598068 | 6/2013 |
| EP | 2598069 | 6/2013 |
| WO | WO-9220291 | 11/1992 |
| WO | WO-9525472 | 9/1995 |
| WO | WO-9736548 | 10/1997 |
| WO | WO-9962413 | 12/1999 |
| WO | WO-0062699 | 10/2000 |
| WO | WO-0122897 | 4/2001 |

(56) References Cited

FOREIGN PATENT DOCUMENTS

| | | |
|---|---|---|
| WO | WO-0170114 | 9/2001 |
| WO | WO-03082080 | 10/2003 |
| WO | WO-2005041748 | 5/2005 |
| WO | WO-2005110528 | 11/2005 |
| WO | WO-2006041881 | 4/2006 |
| WO | WO-2007008954 | 1/2007 |
| WO | WO-2011082279 | 7/2011 |
| WO | WO-2011119857 | 9/2011 |
| WO | WO-2011130534 | 10/2011 |
| WO | WO-2012068471 | 5/2012 |
| WO | WO-2012075156 | 6/2012 |
| WO | WO-2012130337 | 10/2012 |
| WO | WO-2012131107 | 10/2012 |
| WO | WO-2012158864 | 11/2012 |
| WO | WO-2013028812 | 2/2013 |
| WO | WO-2013055815 | 4/2013 |
| WO | WO 2013070724 | 5/2013 |

OTHER PUBLICATIONS

U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency catheter ablation of accessory pathways in infants." Heart, 78:160-162 (1997).
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Gelfand, M., et al., "Treatment of renal failure and hypertension." U.S. Appl. No. 60/442,970, 2003.
Hall, W. H., et al. "Combined embolization and percutaneous radiofrequency ablation of a solid renal tumor." Am. J. Roentgenol,174: 1592-1594 (2000).
Han, Y.-M, et al., "Renal artery ebolization with diluted hot contrast medium: An experimental study." J Vasc Interv Radiol, 12: 862-868 (2001).
Hanson, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustgarten, D.L.,et al., "Cryothermal ablation: Mechanism of tissue injury and current experience in the treatment of tachyarrhythmias." Progr Cardiovasc Dis, 41:481-498 (1999).
Medical-Dictionary.com, Definition of "Animal Model," http://medical-dictionary.com (search "Animal Model"), 2005.
Medtronic, Inc., Annual Report (Form 10-K) (Jun. 28, 2011).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Weinstock, M., et al., "Renal denervation prevents sodium retention and hypertension in salt sensitive rabbits with genetic baroreflex impairment." Clinical Science, 90:287-293 (1996).
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013.
ClinicalTrials.gov, Renal Denervation in Patients with uncontrolled Hypertension in Chinese (2011), www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A.., "Endovascular Skills—Guidewires, Catheters, Arteriography, Balloon Angioplasty, Stents", pp. 70-71, 101 and 188-190 (1998).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006).
Mount Sinai School of Medicine clinical trial for Impact of Renal Sympathetic Denervation of Chronic Hypertension, Mar. 2013, http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Oz, Mehmet, Pressure Relief, Time, Jan. 9, 2012, 2 pages. <www.time.come/time/printout/0,8816,2103278,00.html>.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Pulmonary Vein Stenosis Following Catheter Ablation of Atrial Fibrillation, Curr. Opin. Cardio. 20 :484-490, 2005.
Papademetriou, Vasilios, Renal Sympathetic Denervation for the Treatment of Difficult-to-Control or Resistant Hypertension, Int. Journal of Hypertension, 2011, 8 pages.

(56) References Cited

OTHER PUBLICATIONS

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009.

Schlaich, M.P. et al., "Renal Denervation as a Therapeutic Approach for Hypertension: Novel Implictions for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

USRDS United States Renal Data System 2003 Annual Data Report.

Valente, John F. et al., "Laparoscopic Renal Denervation for Intractable ADPKD-Related Pain", Nephrol Dial Transplant (2001) 16:160.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

European Search Report dated May 3, 2012; European Patent Application No. 11192511.1; Applicant: Ardian, Inc. (6 pages).

European Search Report dated May 3, 2012; European Patent Application No. 11192514.5; Applicant: Ardian, Inc. (7 pages).

European Search Report dated Jan. 30, 2013; European Application No. 12180426.4; Applicant: Medtronic Ardian Luxembourg S.A.r.l.; 6 pages.

European Search Report dated Feb. 28, 2013; Application No. 12180427.2; Applicant: Medtronic Ardian Luxembourg S.A.r.l.; 4 pages.

European Search Report dated Jan. 30, 2013; Application No. 12180428.0; Applicant: Medtronic Ardian Luxembourg S.A.r.l.; 6 pages.

European Search Report dated Jan. 30, 2013; Application No. 12180430.6; Applicant: Medtronic Ardian Luxembourg S.A.r.l.; 6 pages.

European Search Report dated Jan. 30, 2013; Application No. 12180431.4; Applicant: Medtronic Ardian Luxembourg S.A.r.l.; 6 pages.

European Search Report dated Feb. 22, 2013; Application No. 12180432.2; Applicant: Medtronic Ardian Luxembourg S.A.r.l.; 6 pages.

* cited by examiner

*Arterial Vasculature*

*Venous Vasculature*

NEUROMODULATION CATHETERS AND ASSOCIATED SYSTEMS AND METHODS

TECHNICAL FIELD

The present technology relates generally to renal neuromodulation catheters and associated systems and methods. In particular, several embodiments are directed to energy-emitting catheters for intravascular renal neuromodulation and to associated systems and methods.

BACKGROUND

The sympathetic nervous system (SNS) is a primarily involuntary bodily control system typically associated with stress responses. Fibers of the SNS innervate tissue are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys of plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

DETAILED DESCRIPTION

Figure 1:
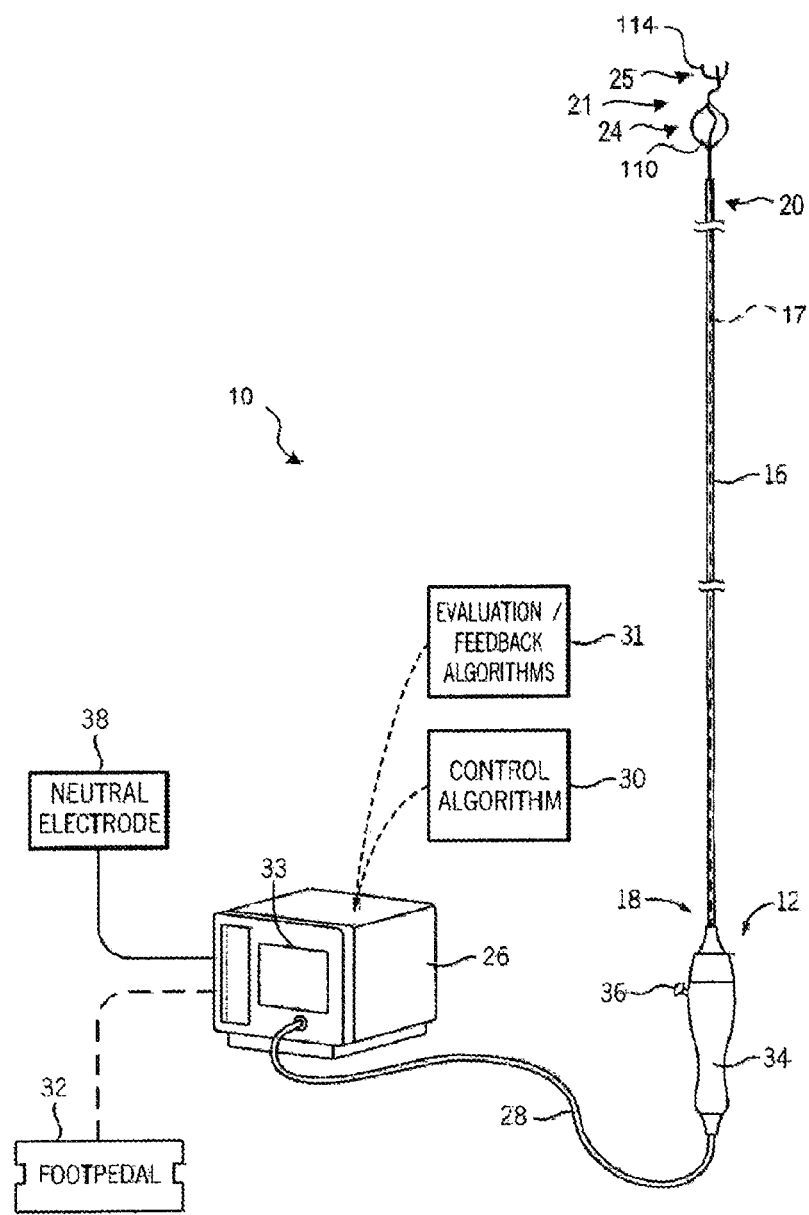
FIG. 1 illustrates an intravascular renal neuromodulation system configured in accordance with an embodiment of the present technology.

The present technology is directed to catheters, systems, and methods for achieving electrically- and/or thermally-induced renal neuromodulation (i.e., rendering neural fibers that innervate the kidney inert or inactive or otherwise completely or partially reduced in function) by percutaneous transluminal intravascular access. In particular, at least some embodiments of the present technology relate to catheters, systems, and methods that incorporate a catheter treatment device having at least one energy delivery device transformable between a delivery state and a deployed state. The energy delivery device can be configured to deliver energy (e.g., electrical energy, radio frequency (RF) energy, thermal energy, or combinations thereof) to target tissue after being advanced via catheter along a percutaneous transluminal path (e.g., a femoral artery puncture, an iliac artery and the aorta, a radial artery, or another suitable intravascular path). The energy delivery device is sized and shaped so that electrode regions contact an interior wall of the renal artery when the energy delivery device is in the deployed state (e.g., expanded) within the renal artery. Blood can flow through the expanded energy delivery device since no occlusion of the renal artery occurs intentionally during energy delivery. Further, blood can flow around the energy delivery device to cool the associated electrode regions and/or surrounding tissue. In some embodiments, cooling the electrode regions and/or tissue allows for the delivery of higher power levels at lower temperatures than may be reached without cooling to help create deeper and/or larger lesions during therapy, reduce intimal surface temperature, and/or allow longer activation times with reduced risk of overheating tissue during treatment.

Specific details of various embodiments of the technology are described below with reference to FIGS. 1-16B. Although many of the embodiments are described below with respect to catheters, systems, and methods for intravascular modulation of renal nerves using energy delivery devices, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-16B.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

I. RENAL NEUROMODULATION

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the down regulation of sympathetic drive that accompanies renal neuromodulation.

Various techniques can be used to partially or completely incapacitate neural pathways, such as those innervating the kidney. The purposeful application of energy (e.g., electrical energy, RF energy, pulsed electrical energy, thermal energy, or combinations thereof) to tissue by energy delivery element(s) can induce one or more desired thermal heating effects on localized regions of the renal artery and adjacent regions of the renal plexus, which lay intimately within or adjacent to the adventitia of the renal artery. The purposeful application of the thermal heating effects can achieve neuromodulation along all or a portion of the renal plexus.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

II. SELECTED EMBODIMENTS OF CATHETERS

FIG. 1 illustrates a renal neuromodulation system 10 configured in accordance with an embodiment of the present technology. System 10 includes an intravascular catheter 12 operably coupled to an energy source or energy generator 26. In the embodiment shown in FIG. 1, catheter 12 includes an elongate hollow shaft 16 having a distal portion 20 and a handle 34 affixed to a proximal shaft portion 18. Catheter 12 further includes a therapeutic assembly in the form of an intraluminal energy delivery device 21 slidably disposed within and extendable from shaft distal portion 20 and including a first proximal electrode array 110 and a second distal electrode array 114. Energy delivery device 21 is affixed to or is integrally formed (i.e. without joints) as a part of the distal end of a control rod 17 extending slidably through a lumen within catheter shaft 16. As explained in further detail below, energy delivery device 21 is configured to be delivered to a renal blood vessel in a low-profile state while radially constrained within shaft distal portion 20. Upon reaching a target treatment site within the renal blood vessel, energy delivery device 21 is ejected from the open distal end 150 of shaft 16 whereupon it tends to self-recover into a preformed radially expanded state for apposition against the vessel wall to deliver energy at the treatment site and for providing therapeutically-effective renal neuromodulation such as electrically- and/or thermally-induced neuromodulation. Where the respective struts or fingers are bowed or splayed to contact the wall of the renal blood vessel, electrode arrays 110, 114 define electrode regions 24, 25 thereof that transmit energy to the renal blood vessel wall. Energy delivery device 21 may be transformed between the collapsed and expanded states by axial translation of control rod 17 within shaft 16 through manual actuation of a knob, a pin, or a lever such as an actuator 36 operatively connected to control rod 17 and carried by handle 34.

Energy generator 26 is electrically coupled to catheter 12 via a cable 28 and is configured to produce a selected form and magnitude of energy for delivery to the target treatment site via energy delivery device 21. Control rod 17 may be in electrical communication with cable 28 to also function as a conductor for energy delivery device 21. Alternatively, a separate electrical lead (not shown) may extend through shaft 16 alongside or surrounding control rod 17 to conduct electricity from cable 28 to energy delivery device 21. The electricity travels through energy delivery device 21 to electrode regions 24, 25 and ultimately to the target treatment site. A control mechanism, such as a foot pedal 32, may be connected (e.g., pneumatically or electrically connected) to energy generator 26 to allow the operator to initiate, terminate and, optionally, adjust various operational characteristics of the generator, including, but not limited to, power delivery. System 10 may also include a wired or wireless remote control device (not shown) that can be positioned in a sterile field and operably coupled to the energy generator 26. In other embodiments, a remote control device may be built into handle assembly 34. Energy generator 26 can be configured to deliver the treatment energy via an automated control algorithm 30 and/or under the control of the clinician. In addition, energy generator 26 may include one or more evaluation or feedback algorithms 31 to provide feedback to the clinician before, during, and/or after therapy.

Figure 2:
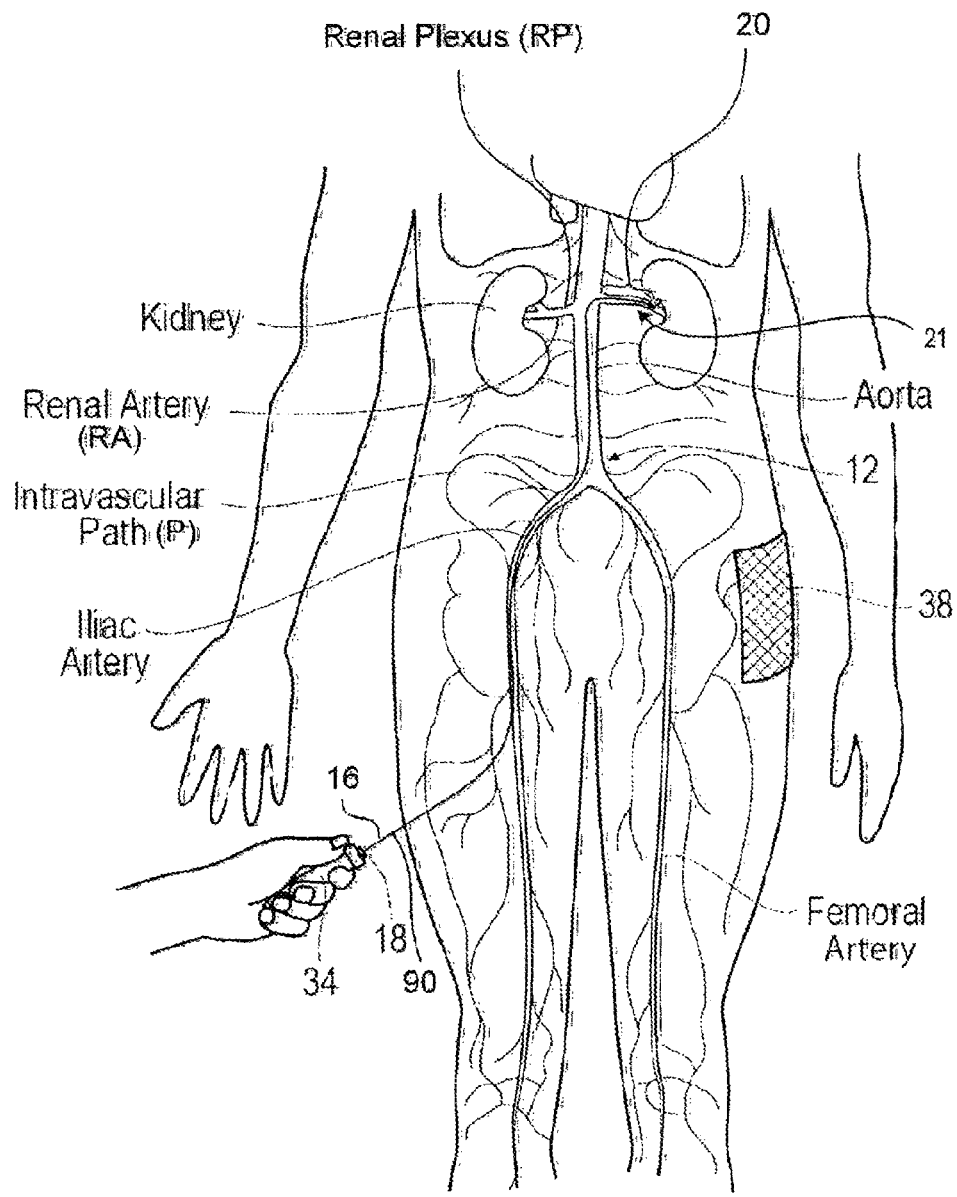
FIG. 2 illustrates modulating renal nerves with a catheter in accordance with an embodiment of the present technology.

System 10 can provide delivery of a monopolar electric field via electrode regions 24, 25 of proximal and distal electrode arrays 110, 114, respectively. In such embodiments, a passive, neutral or dispersive electrode 38 may be electrically connected to energy generator 26 and attached to the exterior of a subject, as shown in FIG. 2. Additionally, catheter 12 can include one or more sensors (not shown), such as one or more temperature (e.g., thermocouple, thermistor, etc.), impedance, pressure, optical, flow, chemical or other sensors.

Energy generator 26 may be part of a device that includes processing circuitry, such as a microprocessor, and a monitor or display 33. The processing circuitry may be configured to execute stored instructions relating to control algorithm 30. The microprocessor may be configured to communicate with catheter 12 (e.g., via cable 28) to control power to energy delivery device 21 and/or to obtain signals from any sensors. The microprocessor may be configured to provide indications of power levels or sensor data, such as audio, visual (e.g., on monitor 33) or other indications, or may be configured to communicate the information to another device. For example, energy generator 26 may also be configured to be operably coupled to a laboratory monitor or system for displaying treatment information.

Figure 14:
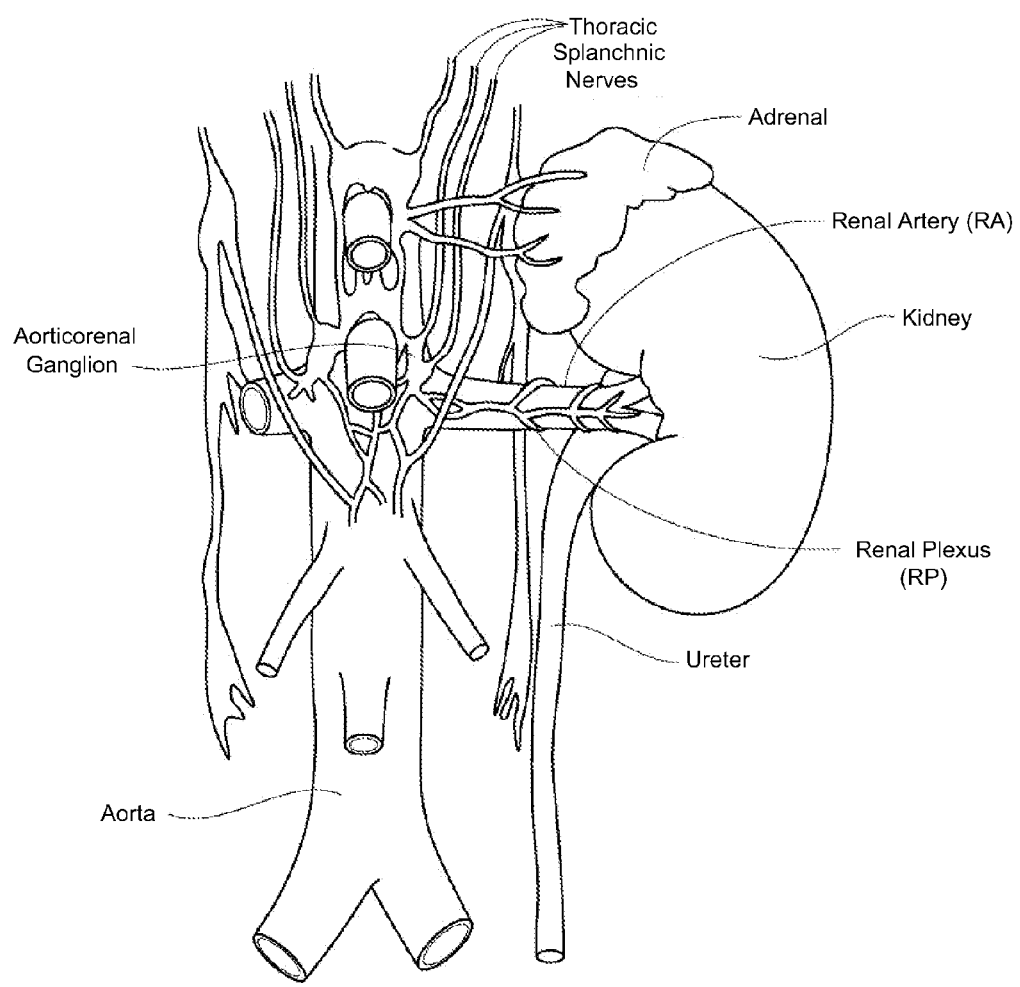
FIG. 14 is an anatomic view of nerves innervating a left kidney to form the renal plexus surrounding the left renal artery.

FIG. 2, with additional reference to FIG. 14, illustrates modulating a human subject's renal nerves with an embodiment of catheter 12, which provides access to the renal plexus RP through an intravascular path P extending from a percutaneous access site such as a femoral (illustrated), brachial, radial, or axillary artery to a targeted treatment site within a respective renal artery RA. As illustrated schematically, a guiding catheter 90 may be used to provide a conduit from outside the subject to a location adjacent the target site. Catheter 12 is inserted through guiding catheter 90 with proximal shaft portion 18 remaining exposed proximally of the guiding catheter. By manipulating proximal shaft portion 18 from outside the subject, the clinician may advance catheter 12 through the sometimes tortuous intravascular path P and position distal shaft portion 20 at least partially inserted within renal artery RA for deployment of energy delivery device 21, as will be described in detail below. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation of catheter 12. Further, in some embodiments, image guidance components (e.g., IVUS, OCT) may be incorporated into catheter 12 itself.

Figure 3A:
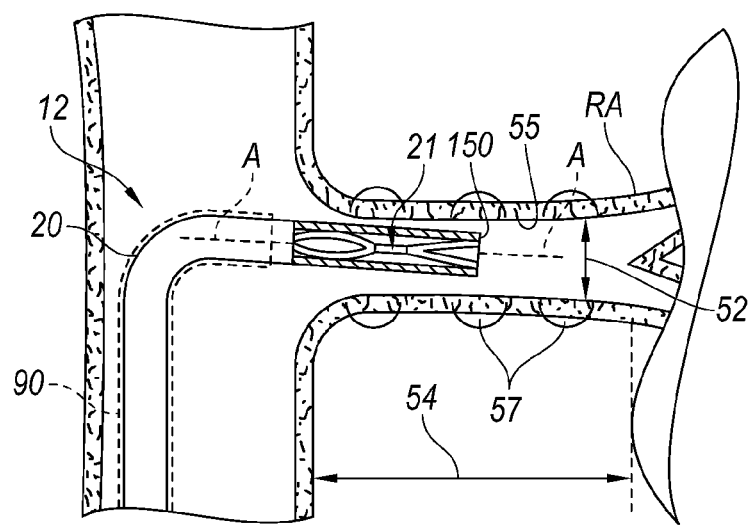
FIG. 3A is a partial cross-section of a distal portion of a renal neuromodulation system positioning an energy delivery device in a low-profile state within a renal artery of a patient in accordance with an embodiment of the technology.
Figure 3B:
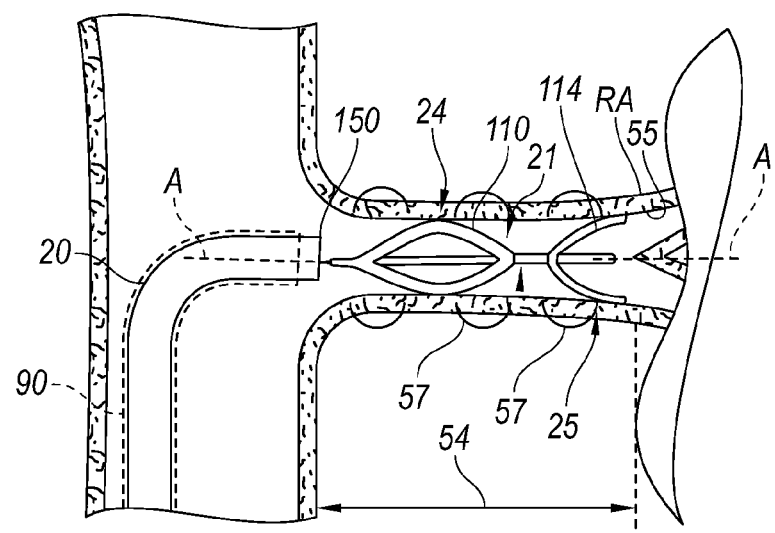
FIG. 3B is a partial cross-section of the distal portion of the renal neuromodulation system of FIG. 3A showing the energy delivery device in a deployed state in accordance with an embodiment of the technology.

FIGS. 3A and 3B illustrate the delivery of an embodiment of energy delivery device 21 to a renal artery RA of a patient. The patient's typical contralateral renal artery is omitted for clarity. Referring first to FIG. 3A, self-expanding energy delivery device 21 is shown radially constrained within distal portion 20 of catheter shaft 16 in a delivery state having a low-profile diameter or transverse dimension. In the illustrated embodiment, catheter 12 extends through guide catheter 90 (shown in phantom) such that at least a distal segment of distal shaft portion 20 protrudes from guide catheter 90 into the lumen of renal artery RA. The distal end of guide catheter 90 is sized and shaped to fit within at least the ostium of the renal artery RA. For example, guide catheter 90 can have an outer diameter that is less than a renal artery inner diameter 52.

Referring next to FIG. 3B, energy delivery device 21 is shown having been exposed or ejected from catheter distal shaft portion 20 and thus permitted to radially self-expand towards its pre-formed deployed state until electrode regions 24, 25 of proximal and distal electrode arrays 110, 114 make stable contact with an inner surface of the wall 55 of the artery RA. To release energy delivery device 21 from distal shaft portion 20 into the target treatment site, shaft 16 and control rod 17 are longitudinally translated with respect to each other, as by operation of actuator 36. In a first exemplary embodiment, energy delivery device 21 may be held in a fixed position with respect to the renal artery RA by control rod 17 which may be affixed to handle 34. Actuator 36 may be operated to retract catheter shaft 16 over control rod 17, thus exposing energy delivery device 21. In this embodiment, energy delivery device 21 can expand radially without longitudinal movement within the renal artery RA, thereby preventing potential abrasion of vessel wall 55 or unwanted engagement with the bifurcation of the renal artery. In a second exemplary embodiment, catheter shaft 16 may be held in a fixed position with respect to the renal artery RA by attachment of its proximal portion 18 to handle 34. Actuator 36 may be operated to expel energy delivery device 21 from the open distal end 150 of distal shaft portion 20 by advancing control rod 17 within catheter shaft 16.

A maximum axial length of deployed energy delivery device 21 of FIG. 3B can be approximately equal to or less than a length 54 of a main renal artery RA (i.e., a section of a renal artery proximal to a bifurcation). The dimensions of the energy delivery device 21 can be selected based, at least in part, on the dimensions of a patient's anatomy and the location of the treatment site. In an embodiment, each of electrode arrays 110, 114 can be configured to provide three points or zones of tissue contact, which define electrode regions 24, 25 respectively. In other embodiments, electrode arrays 110, 114 can each have more than three struts to provide more than three points of contact. Electrode arrays 110, 114 can provide sufficient contact forces between electrode regions 24, 25 and the vessel wall 55 for effective energy delivery to the artery wall to provide lesion formation. Additionally, the lesions created by electrode regions 24, 25 can be at discrete locations to minimize or avoid problems that may be associated with forming a continuous lesion in a single transverse plane about the entire circumference of the vessel wall 55. Blood can flow through the cells formed between the struts of first electrode array 110 and through the cells formed between the fingers of distal electrode array 114 when the arrays are in their expanded states, as shown in FIG. 3B. If necessary to avoid occlusion or "wedging" of the vessel, the distal tip of guide catheter 90 can be withdrawn from the renal ostium during the treatment. The flowing blood can absorb thermal energy to reduce the temperatures of energy-emitting struts or fingers (including the active regions 24, 25) and other portions of energy delivery device 21 and/or adjacent vessel wall 55 to facilitate the therapy, as for example by permitting higher energy emission and/or longer treatment times.

Once electrode regions 24, 25 make proper tissue contact, the purposeful application of energy from energy delivery device 21 may be applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

Figure 4A:
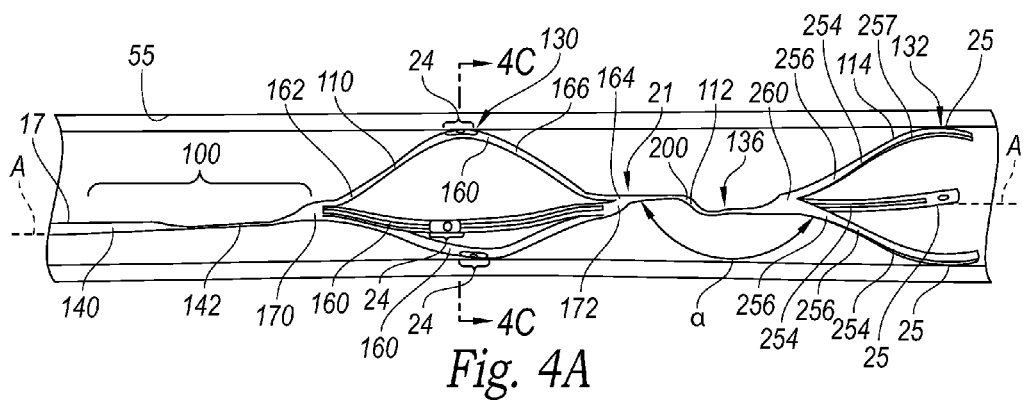
FIG. 4A is a longitudinal partial cross-section of an energy delivery device in a deployed state within a renal artery of a patient in accordance with an embodiment of the technology.
Figure 4B:
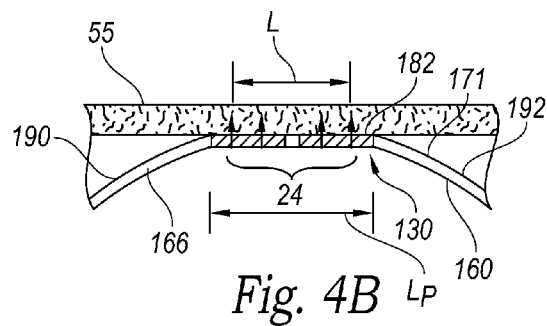
FIG. 4B is an enlarged longitudinal cross-section of a tissue contacting portion of a strut of the device of FIG. 4A in accordance with an embodiment of the technology.

The neuromodulating effects are generally a function of, at least in part, power (e.g. watts), time, stability of contact between electrode regions 24, 25 and the vessel wall (as shown in FIGS. 3B and 4A), and blood flow through the vessel. The neuromodulating effects may include denervation, thermal ablation, and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

As described previously, the illustrated embodiment of system 10 can be operated in a monopolar or unipolar mode where the return path for the applied electric field is established, e.g., by external dispersive or neutral electrode 38. The monopolar application of RF electric field energy serves to ohmically or resistively heat tissue in the vicinity of electrode regions 24, 25 to thereby thermally injure the targeted tissue. The treatment objective is to thermally induce neuromodulation (e.g., necrosis, thermal alteration or ablation) in the targeted neural fibers. The thermal injury forms a lesion in the vessel wall. Alternatively, a RF electrical field may be delivered with an oscillating or pulsed intensity that does not thermally injure the tissue whereby neuromodulation in the targeted nerves is accomplished by electrical modification of the nerve signals.

FIG. 4A is a side view of energy delivery device 21 in a deployed state within the renal artery RA. Energy delivery device 21 can include a first connection portion 112 disposed between first electrode array 110 and second electrode array 114. A proximal portion 100 of energy delivery device 21 is fixedly coupled to or may be an integrally formed part (i.e. without joints) of control rod 17. With energy delivery device 21 in the deployed state as shown in FIG. 4A, electrode arrays 110, 114 tend to relax to their radially expanded, pre-formed configurations having diameters or transverse dimensions greater than RA inner diameter 52 such that arrays 110, 114 maintain apposition with the wall 55 of the renal artery RA. As described previously, electrode arrays 110, 114 are configured to provide circumferentially discontinuous contact between energy delivery device 21 and the vessel wall 55. With energy delivery device 21 in a deployed state, electrode regions 24 of first electrode array 110 are defined at bowed strut apices or peak portions 130 and electrode regions 25 of second electrode array 114 are similarly defined at splayed fingertip portions 132. First connection portion 112 may be considered a narrow waist 136 disposed between expanded arrays 110, 114. A section of vessel wall 55 of the renal artery RA disposed between expanded strut peak portions 130 and expanded fingertip portions 132 is radially spaced from first connection portion 112.

In the illustrated embodiment of FIG. 4A, a proximal strut junction 170 of energy delivery device 21 is coupled to control rod 17 by a proximal portion 100 that includes a tubular retainer portion 140 and a second connection portion 142. Retainer portion 140 fixedly receives the distal end of control rod 17 therewithin and can include, without limitation, one or more slots, apertures, connectors (e.g., threaded connectors, snap connectors, etc.), or other features for coupling to control rod 17. Second connection portion 142 is more flexible than retainer portion 140 or proximal strut junction 170. As described above, energy delivery device 21 is alternatively formed as an integral part or extension (e.g. without joints) of control rod 17, thus eliminating the need for retainer portion 140.

Energy delivery device 21 can have an integral one-piece construction and can be formed by cutting (e.g., laser cutting) a metal tube such as a slender, thin-walled hypodermic tube ("hypotube"). After cutting the tube to a defined pattern, struts 160 and fingers 254 are forced radially outward, as by inserting a temporary mandrel or other form. The entire energy delivery device 21 then is heat treated to take on the size and shape of a radially expanded basket in the case of electrode array 110 and radially expanded splayed fingers in the case of electrode array 114. Typically, the specific geometry of first connection portion 112 is obtained during cutting of the starting tube. Alternatively, first connection portion 112 may be held in a different configuration such that, during heat treatment it will assume a non-linear shape such as articulation feature 200. In some embodiments, energy delivery device 21 may comprise a metal frame structure with all bare metal surfaces. The entire energy delivery device 21 can be capable of serving as a continuous electrode, although only electrode regions 24, 25 are expected to contact tissue for localized transmission of energy during treatment. Energy can be delivered only through the contact interfaces between electrode regions 24, 25 and the vessel wall 55 to limit the area of contact and limit radially directed forces applied to the wall 55 to control or avoid unwanted responses (e.g., vasospasm). Alternatively, as better described in detail below, the metal frame structure surface can be insulated except for specific limited electrode regions.

Energy delivery device 21 can be made, in whole or in part, of a stress-induced martensite (SIM) material, such as nickel titanium (nitinol), or spring-temper medical grade stainless steel, or age-hardenable ultra high strength "superalloy" metal comprising nickel, cobalt, chromium and molybdenum. Control rod 17 can be made of the above metals in the form of a solid wire or rod, or of thin-walled hollow tubing or a combination of solid and hollow portions. First electrode array 110 can be pre-formed in the shape of an ellipsoid, a prolate spheroid, or the like. The illustrated first electrode array 110, for example, includes three elongate struts 160 that, in the expanded configuration define three closed cells therebetween. Additionally, struts 160 can apply substantially equal outwardly directed forces to the vessel wall 55 to ensure that first electrode array 110 is properly centered in the renal artery without reaching an undesired stress level in the vessel wall. Each strut 160 includes a flexible main body 166 extending longitudinally and, when array 110 is in the preformed basket configuration, curving outwardly between a strut proximal end 162 and a strut distal end 164. Strut proximal ends 162 converge to form proximal strut junction 170 and strut distal ends 164 converge to form distal strut junction 172. Each strut main body 166 may include a pair of parallel spaced-apart arms 173, 175 (FIG. 4C) and a continuous, integral electrode region 24 formed at peak 130 including material of arms 173, 175 and material spanning the space therebetween. Strut main body 166 has a substantially arcuate preformed configuration bowed away from the longitudinal axis A-A of energy delivery device 21. It will be appreciated that the description of one of struts 160 applies equally to the other struts 160 unless the context clearly dictates otherwise.

When first electrode array 110 is in the radially expanded configuration, electrode regions 24 may have atraumatic configurations to limit or minimize injury or trauma to the vessel wall 55 and, in some embodiments, may include generally flat tissue-contacting regions. Electrode regions 24 may be positioned at peak portion 130 between sloped regions 190, 192 (FIG. 4B), which are configured to slide smoothly and atraumatically along tissue to permit repositioning of electrode regions 24, if desired, without initially collapsing first electrode array 110. An outward-facing surface 171 of strut main body 166 can extend continuously and uninterruptedly between strut proximal and distal ends 162, 164 (FIG. 4A) to slide smoothly along tissue and into the open distal end 150 of shaft 16 (FIGS. 3A and 3B) to facilitate collapse and retrieval of energy delivery device 21. In some embodiments, peak portions 130 may have other configurations to help, for example, reduce or prevent movement of electrode regions 24 during energy delivery.

Second electrode array 114 can be pre-formed with cantilevered fingers 254 flared or splayed apart from finger junction 260 in the general shape of a cone, preferably with distal fingertip portions 132 curled inward at least to be substantially parallel with longitudinal axis A-A of energy delivery device 21. The illustrated second electrode array 114, for example, includes three elongate fingers 254 that, in the expanded configuration define three open cells therebetween. Additionally, fingers 254 can apply substantially equal outwardly directed forces to the vessel wall 55 to ensure that second electrode array 114 is properly centered in the renal artery without reaching an undesired stress level in the vessel wall 55. Each finger 254 includes a flexible main body 257 that extends longitudinally and, when array 114 is in the preformed splayed configuration, each finger curves outwardly from a finger proximal end 256. The plurality of finger proximal ends 256 converges to form finger junction 260. Each finger main body 257 may include a pair of parallel spaced-apart arms 273, 275 and a continuous, integral electrode region 25 formed at fingertip portion 132 including material of arms 273, 275 and material spanning the space therebetween. It will be appreciated that the description of one of fingers 254 applies equally to the other fingers 254 unless the context clearly dictates otherwise.

Fingertip portion 132 can have an atraumatic configuration to limit or minimize injury or damage to the vessel wall 55 and, in some embodiments, tissue-contacting electrode regions 25 are generally flat. In other embodiments, however, the second electrode array 114 may have a different configuration and/or include different features. Each fingertip portion 132 may terminate at the distal end of an electrode region 25, or each fingertip portion 132 may extend slightly beyond an electrode region 25 to provide a truncated distal sloped region similar to region 192 flanking peak portion 130 in array 110. An external surface of finger main body 257 can extend continuously and uninterruptedly between finger proximal and distal ends 256, 258 (FIG. 4A) to slide smoothly along tissue and into the open distal end 150 of shaft 16 (FIGS. 3A and 3B) to facilitate collapse and retrieval of energy delivery device 21. Each electrode region 24, 25 has an active zone or area capable of being placed in intimate contact with the vessel wall 55 and delivering energy (represented by arrows in FIG. 4B). The size and shape of the active area can be selected to, for example, thermally affect the targeted tissue 57 (e.g., neural tissue, neural fibers, etc.) shown in FIGS. 3A and 3B, to produce lesions having desired sizes or locations (e.g., depth) or the like.

Figure 4C:
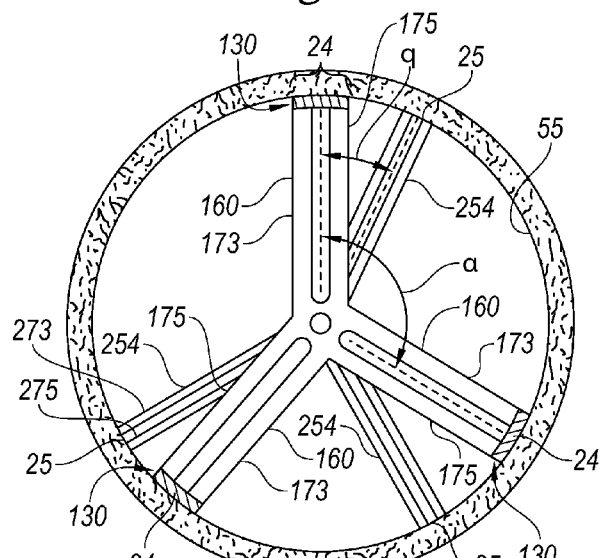
FIG. 4C is a transverse cross-section of the energy delivery device of FIG. 4A taken along line 4C-4C of FIG. 4A.

FIG. 4C is a transverse cross-sectional view of energy delivery device 21 taken along a line 4C-4C of FIG. 4A, wherein electrode regions 24 are shown to be approximately evenly spaced about the circumference of wall 55 of the renal artery. In the embodiment of FIG. 4C that includes three struts 160, each pair of adjacent struts 160 can define an angle α therebetween that ranges from about 100 degrees to about 140 degrees, and is preferably about 120 degrees. Electrode regions 24 of first electrode array 110 can be circumferentially offset from electrode regions 25 of second electrode array 114 relative to the longitudinal axis A-A such that electrode regions 24 are not longitudinally aligned with electrode regions 25. The angle of offset θ can be selected based on the characteristics of the wall 55, the number of struts 160 and fingers 254, the longitudinal separation of the arrays of electrode regions 24, 25, the desired lesion formation, or other design parameters that may be considered useful. In some embodiments, the angle of offset θ is about 60 degrees to position energy-emitting region 25 circumferentially midway between a pair of electrode regions 24. In other embodiments, the angle of offset θ can be about 0 degrees to align electrode regions 24 with electrode regions 25.

Figure 5:
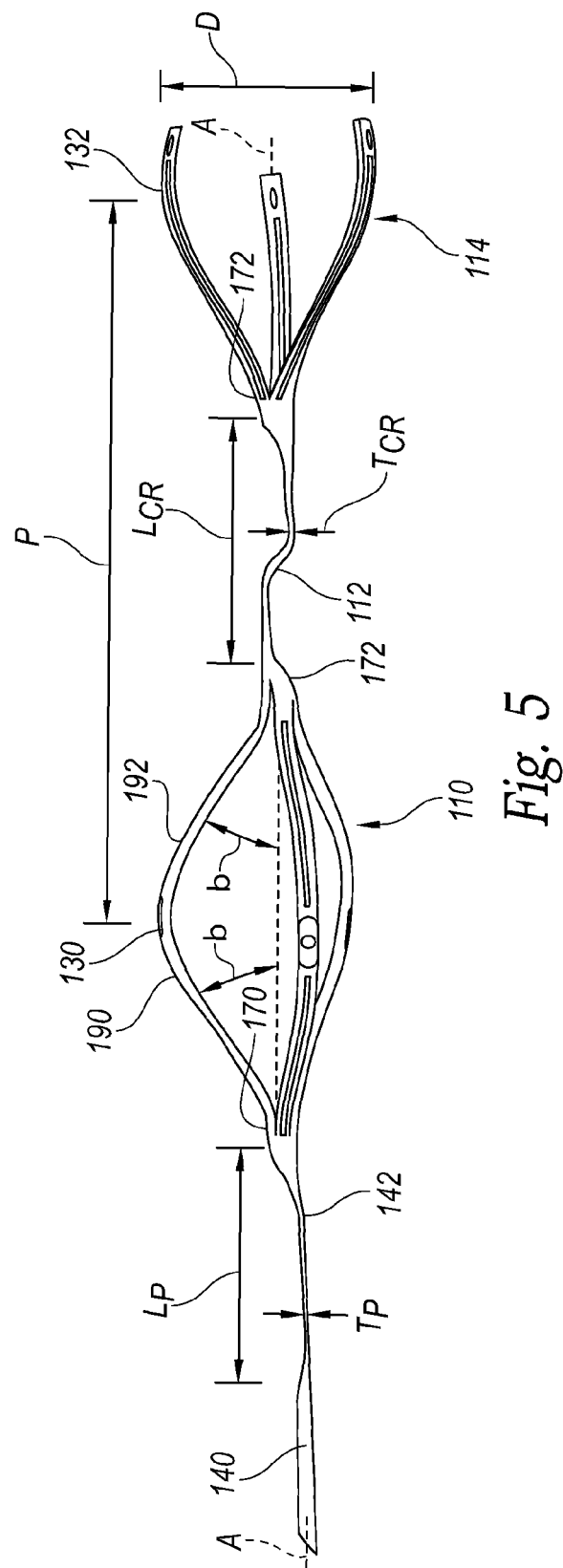
FIG. 5 is a side view of an energy delivery device in a deployed state outside a patient in accordance with an embodiment of the technology.

FIG. 5 is a side view of energy delivery device 21 in a free, unconstrained state outside a patient. Transverse outer dimension D is the minimum diameter of a round hole or bore into which electrode arrays 110 and/or 114 will fit without causing radial contraction of the array(s). Dimension D may range from about 4 mm to about 6 mm depending on the dimensions of the target blood vessel. In one embodiment, for example, outer dimension D is about 5 mm. In the delivery state (FIG. 3A), energy delivery device 21 is radially constrained to an outer dimension that can be substantially less than about 3 mm. For vessels narrowing in the distal direction, first electrode array 110 can be configured to define an expanded outer dimension that is larger than the expanded outer dimension of second electrode array 114. For vessels widening in the distal direction, first electrode array 110 can be configured to define an expanded outer dimension that is smaller than the expanded outer dimension of second electrode array 114. The outer dimensions to which energy delivery device 21 tends to elastically return when in the deployed state are somewhat larger than the expected lumen diameter of the renal artery such that peak portions 130, 132 are pressed against the vessel wall 55 with a sufficient force to maintain electrical contact without mechanically injuring the wall tissue. In other embodiments, energy delivery device 21 may have different dimensions.

Second connection portion 142 of proximal portion 100 can have an axial length $L_P$ in a range of about 4 mm to about 8 mm and a wall thickness $T_P$ defined by the starting tubing in a range of about 0.08 mm to about 0.35 mm. Second connection portion 142 can have a transverse width $W_P$ in a range of about 0.08 mm to about 0.40 mm (See FIG. 9). In some embodiments, the axial length $L_P$ is about 5 mm, 6 mm, or 7 mm, and the width $W_P$ is about 0.28 mm. A pitch P, defined as a distance between peak 130 and fingertips 132 measured parallel to the longitudinal axis A-A can be in a range of about 5 mm to about 20 mm. In some embodiments, pitch P is in a range of about 11 mm to about 15 mm. With the illustrated embodiment of energy delivery device 21 in the deployed state, the angles formed between axis A-A and sloped regions 190, 192 of struts 166 can be in a range of about 50 degrees to about 70 degrees. In some embodiments, angle is about 60 degrees. Similar to second connection portion 142, first connection portion 112 can have an axial length $L_{CR}$ in a range of about 4 mm to about 8 mm, a wall thickness $T_{CR}$ in a range of about 0.08 mm to about 0.35 mm, and a similar range of widths. The illustrated first connection portion 112 can include a bent wire or portion of a tube with a wall thickness $T_{CR}$ of about 0.20 mm.

Referring back again to FIGS. 3A and 3B, catheter 12, or at least distal portion 20 of catheter shaft 16 can be sufficiently flexible to traverse relatively tortuous vascular paths. As discussed previously, FIG. 3A shows energy delivery device 21 radially constrained in the delivery state by catheter shaft distal portion 20. Catheter distal portion 20 may flex in a substantial fashion to gain entrance into a respective left/right renal artery by following a path defined by guide catheter 90, a guide wire, and/or a sheath. In some embodiments, guide catheter 90 can be a renal guide catheter with a preformed curve along the distal portion to direct elongate catheter shaft 16 from the percutaneous insertion site to the renal artery RA. In another embodiment, catheter 12 may be directed to the treatment site within the renal artery RA by engaging and tracking a guide wire (not shown) that extends from the percutaneous access site into the renal artery RA. In operation, the guide wire can be delivered into the renal artery RA and catheter 12 is then passed over the guide wire into the renal artery RA.

Although the foregoing discussion is primarily directed to the use of the system 10 in the renal blood vessels, the system 10 can be used in different regions of the subject, including the cardiovascular system, respiratory system, digestive system, reproduction system, or other suitable portions of the body. Energy delivery device 21 can be delivered to a wide range of body structures, including the heart, angled vessels (e.g., hollow vessels such as arteries, veins, the urethra, etc.), stomach, trachea, esophagus, intestine, airways, or other structures. The dimensions, configurations, characteristics (e.g., expansion characteristics of expandable features such as electrode arrays), or the like can be selected based on the delivery path, treatment site, and/or energy to be delivered.

Figure 6:
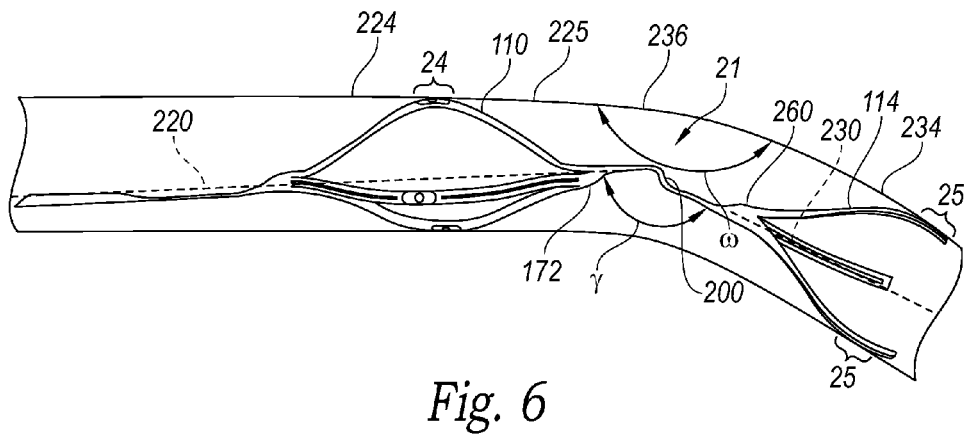
FIG. 6 is a schematic side view of the energy delivery device of FIG. 5 in a deployed state within an angled vessel in accordance with an embodiment of the technology.
Figure 7:
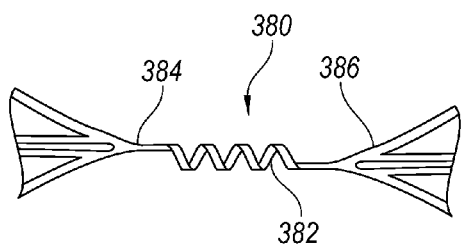
FIG. 7 is a side view of a helical connection portion between first and second electrode arrays in accordance with another embodiment of the technology.

FIG. 6 is a side view of energy delivery device 21 in a deployed state within an angled vessel in accordance with an embodiment of the technology. First connection portion 112 may be a straight, narrow segment (not shown) that is formed by cutting away much of the tubing between arrays 110, 114 during manufacturing. The width of first connection portion 112 can be selected, in conjunction with thickness $T_{CR}$ to provide sufficient flexibility for deployment of energy delivery device 21 in an angled blood vessel, as explained in further detail below. Optionally, the flexibility of first connection portion 112 can be enhanced by including an articulation feature configured to permit substantial bending between electrode arrays 110, 114 and the respective longitudinal axes 220, 230 therethrough. The articulation feature may be selected from a variety of different configurations when energy delivery device 21 is in the delivery state or the deployed state such as offset, arcuate, or kinked shapes, or the partially helical shape of articulation feature 200 illustrated herein. FIG. 7 is a side view of an alternative first connection portion 380 that includes an articulation feature 382 with a helical shape. The number of turns, diameter, pitch, and other aspects can be selected based on the desired characteristics (e.g., spring constant, restorative properties, etc.). Any suitable articulation feature can be achieved using an appropriate pattern when cutting and forming energy delivery device 21, such as from a single metal tube.

If energy delivery device 21 is deployed at a significant bend 236 of an angled vessel 225, then the flexibility of connection portion 112 permits device 21 to bend with negligible force at an angle γ between longitudinal axes 220, 230 to generally match an angle ω defined by bend 236. If connection portion 112 were not sufficiently flexible, then device 21 would tend to cut straight across bend 236 such that electrodes 24, 25 might be misaligned and connection portion 112, distal strut junction 172 and/or finger junction 260 might make undesirable electrical contact with the vessel wall inside of bend 236. Therefore, when connection portion 112 is sufficiently flexible, with or without an articulation region, then longitudinal axis 220 through array 110 can be substantially aligned with a proximal portion 224 of angled vessel 225 and longitudinal axis 230 through array 114 can be substantially aligned with distal portion 234 of angled vessel 225. Energy delivery device 21 can thus accommodate the degrees of vessel curvature likely to be encountered at the intended treatment site such that most or substantially all electrode regions 24, 25 can contact the inner wall of vessel 225 to ensure that a therapeutically effective amount of energy is delivered to the desired wall locations without delivering energy to unintended locations. For example, FIG. 6 shows all of electrode regions 24 contacting proximal portion 224 before bend 236 in the vessel 225 and all of electrode regions 25 contacting distal portion 234 past bend 236 in the vessel 225.

Figure 8:
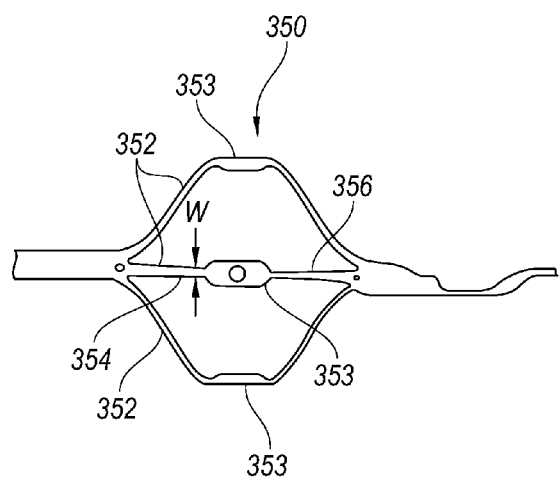
FIG. 8 is a side view of an electrode array in accordance with another embodiment of the technology.

FIG. 8 illustrates an alternative first electrode array 350 including struts 352 with electrode regions 353. Proximal arms 354 and distal arms 356 of struts 352 have relatively narrow widths W to help limit blood flow perturbations through the array, such as turbulent flow and/or eddying. Each electrode region 353 can be wider than arms 354, 356 to provide relatively large active contact area and can have any of a variety of shapes, such as, e.g. polygon, rectangle, square, circle, or ellipse. Each strut 352 can include a single electrode region 353. In other embodiments, however, a plurality of electrode regions can be evenly or unevenly spaced-apart from one another along the struts 352.

Figure 9:
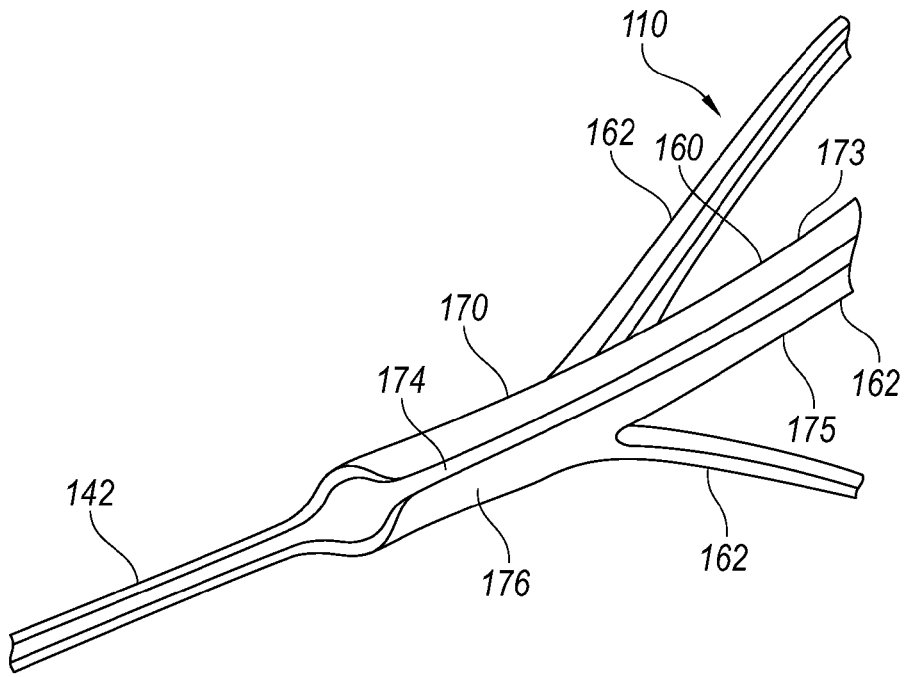
FIG. 9 is an isometric view of a strut junction configured in accordance with an embodiment of the technology.

FIG. 9 is an enlarged isometric view of strut junction 170 wherein first electrode array 110 is in the preformed radially expanded basket configuration. Strut junction 170 comprises a tubular body portion 176 with second connection portion 142 extending proximally therefrom and three strut proximal ends 162 extending distally therefrom. A single longitudinal slot 174 extends fully the length of tubular body portion 176 to increase the flexibility thereof, and slot 174 continues along a first strut 160 to divide the strut into spaced-apart strut arms 173 and 175 as described above. As shown, the other struts 160 also have spaced-apart strut arms 173 and 175. However, the slots in the other struts 160 do not extend through strut junction 170 into tubular body portion 176. It can be readily understood that all of the elements illustrated in FIG. 9 can be formed by cutting away material from a single piece of welded or seamless metal hypodermic tube having the inside and outside diameters of tubular body portion 176. Such a construction can be termed integral or jointless, notwithstanding that the hypodermic tubing may be formed originally (e.g. prior to laser cutting) with a continuous longitudinal weld seam.

Figure 10:
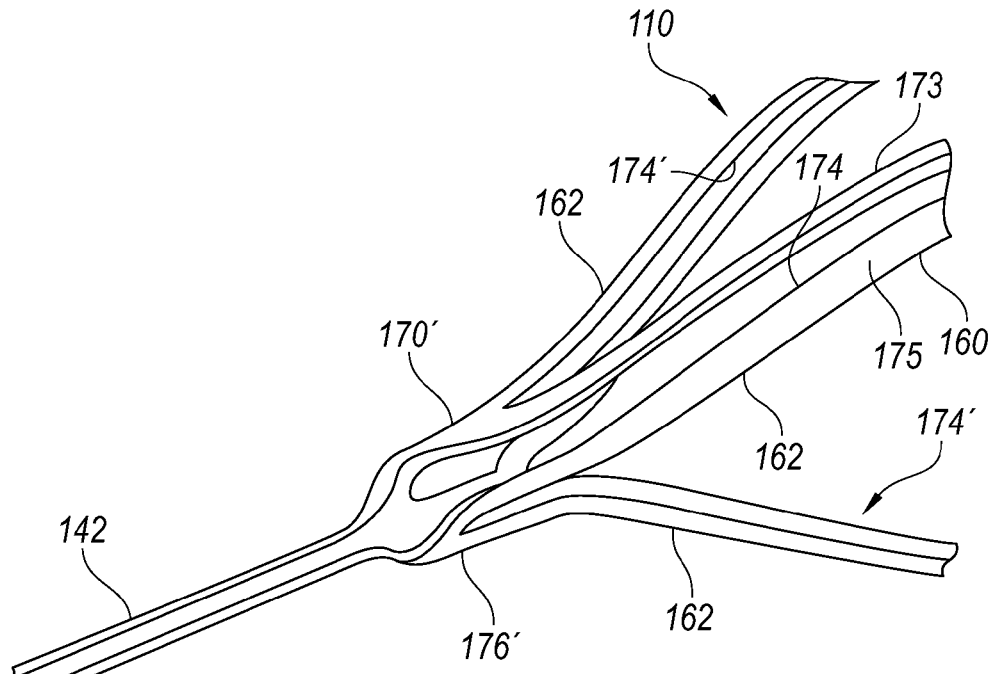
FIG. 10 is an isometric view of an embodiment of a strut junction configured in accordance with another embodiment of the technology.

FIG. 10 is an enlarged isometric view of an alternative embodiment of a strut junction 170' wherein first electrode array 110 is in the preformed radially expanded basket configuration. Strut junction 170' is similar to strut junction 170 shown in FIG. 9. However, tubular body portion 176' is shorter than tubular body portion 176. As described above regarding the embodiment of FIG. 9, a single longitudinal slot 174 extends fully the length of tubular body portion 176' to increase the flexibility thereof, and slot 174 continues along a first strut 160 to divide the strut into spaced-apart strut arms 173 and 175. In strut junction 170', the other two slots 174' in the other struts 160 extend proximally almost the full length of tubular body portion 176' to increase the flexibility of tubular body portion 176'. By reducing the length of tubular body portion 176' and eliminating all tubing material that is not required to form the integral junction between struts 160, strut junction 170' is more longitudinally flexible than strut junction 170, thus providing stress relief between connection portion 142 and struts 160. It should be recognized that other embodiments of strut junctions are possible and are considered to be within the scope of the technology. Furthermore, the embodiments illustrated and described herein regarding strut junctions 170 and 170' are equally applicable to distal strut junction 172 and to finger junction 260.

Figure 11:
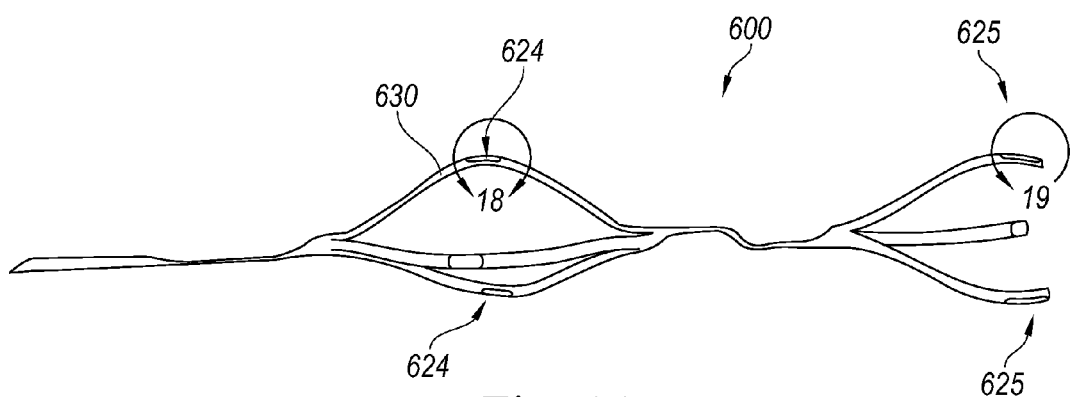
FIG. 11 is a side view of an energy delivery device configured in accordance with another embodiment of the technology.

FIG. 11 is a side view of an energy delivery device 600 configured in accordance with another embodiment of the technology. Energy delivery device 600 is similar to energy delivery device 21 except for the inclusion of an insulator as described herein. Delivery device 600 includes an insulator 630, proximal electrode regions 624, and distal electrode regions 625. Electrode regions 624, 625 can contact and deliver energy to tissue while insulator 630 can prevent energy delivery to undesired tissue locations and can minimize or limit energy losses (e.g., energy losses to surrounding fluid such as blood), clotting or coagulation of blood, or the like. In some embodiments, insulator 630 can be a dielectric material layer covering most of energy delivery device 600 and can include openings or windows at electrode regions 624, 625.

Figure 12:
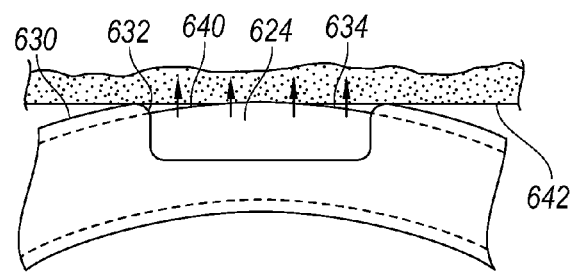
FIG. 12 is a detailed view of a proximal energy-emitting region of the energy delivery device of FIG. 11 in accordance with the embodiment of the technology.

FIG. 12 is a detailed side view of electrode region 624 in accordance with an embodiment of the present technology. The electrode region 624 can be an exposed portion of a support structure 640 (e.g., a metal frame member) positioned to contact a wall 642 of a vessel. Insulator 630 can be formed by coating the entire frame structure 640 via a dipping process. The coating material can comprise an electrical insulating or dielectric material (e.g., a polymer such as polyethylene terephthalate) that inhibits or substantially prevents the delivery of energy from frame assembly 640 to vessel wall 642. Portions of the coating can be removed using an etching process and/or cutting process to define an opening or window 632 facing the wall 642. In other embodiments, insulator 630 may be formed by a shrink wrap process, especially where portions of metal frame member 640 are susceptible to having a shrink tube slipped thereover from one end. For example, insulator 630 can comprise a plurality of polymeric heat shrink tubes applied to frame structure 640. The number, positions, and orientations of the openings or windows of the insulator 630 can be selected to achieve the desired energy delivery.

III. PERTINENT ANATOMY AND PHYSIOLOGY

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal modulation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory catheter.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 13:
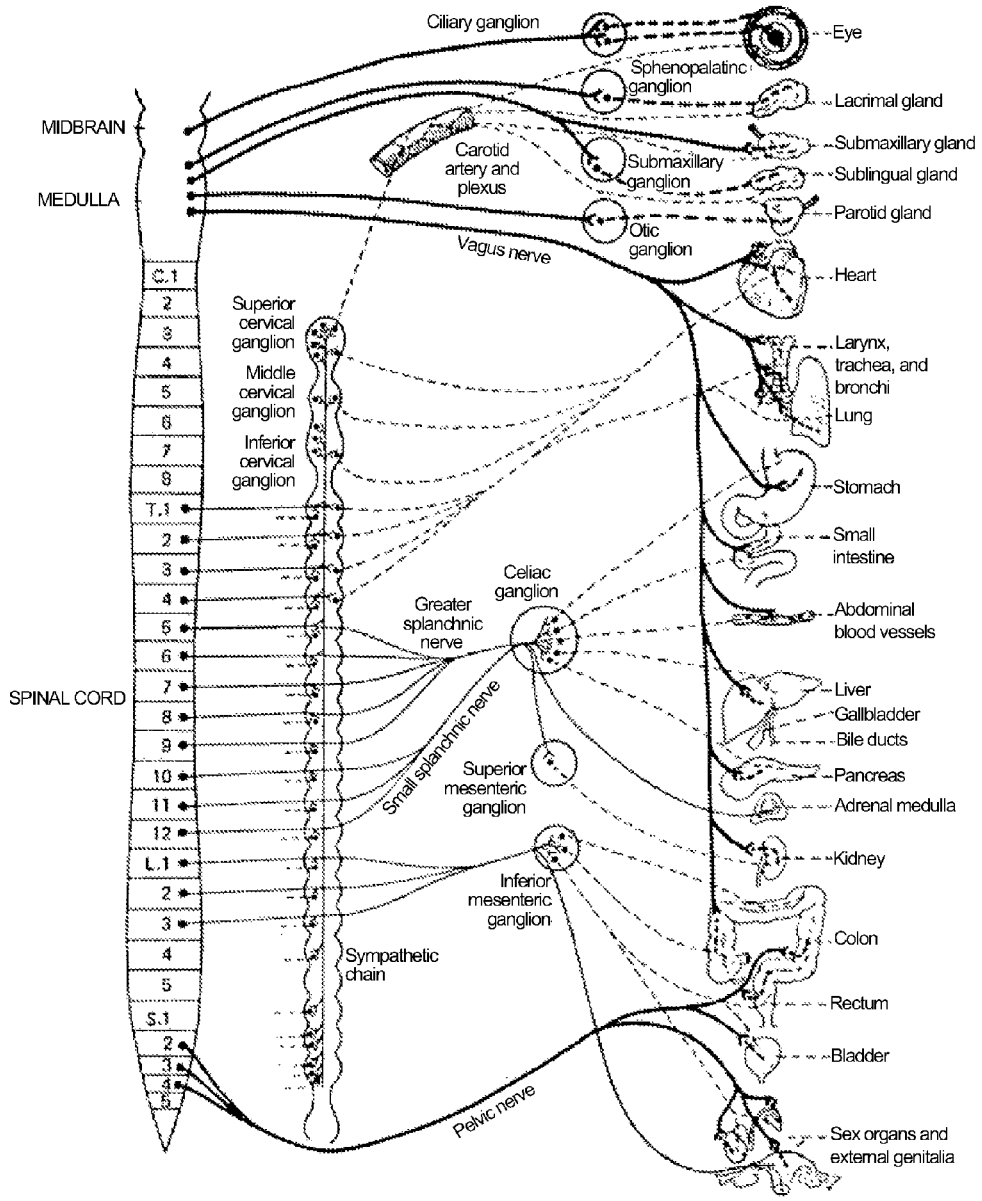
FIG. 13 is a conceptual illustration of the SNS and how the brain communicates with the body via the SNS.

As shown in FIG. 13, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

As shown in FIG. 14, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 15A:
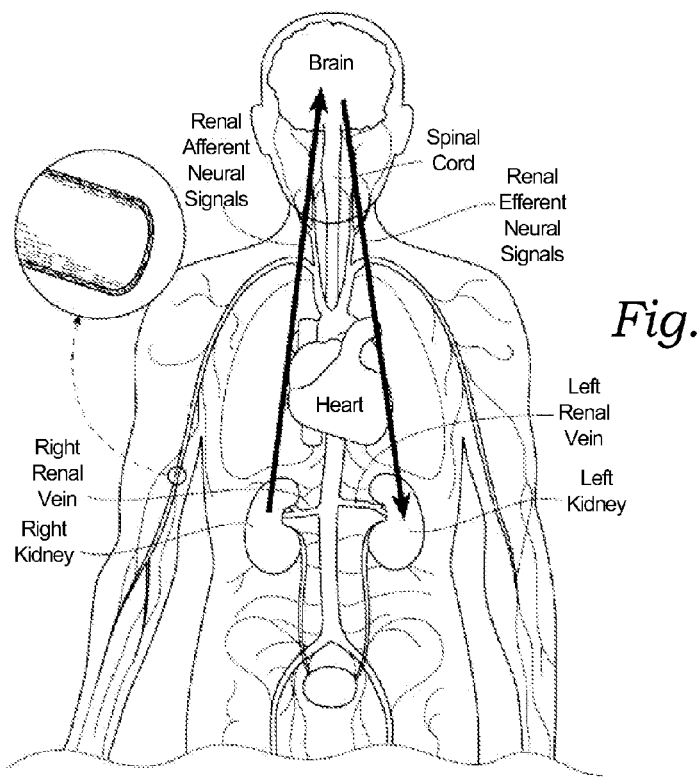
FIGS. 15A and 15B provide anatomic and conceptual views of a human body, respectively, depicting neural efferent and afferent communication between the brain and kidneys.
Figure 15B:
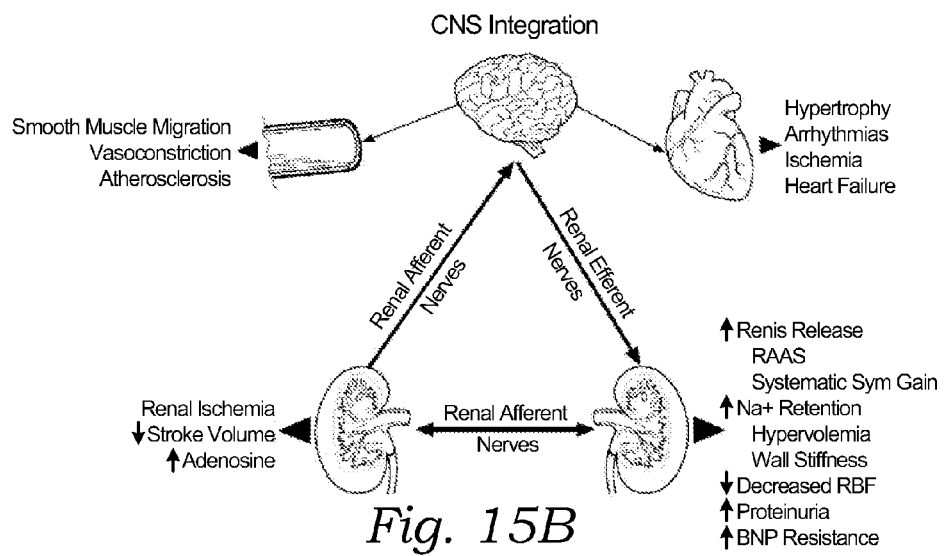

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 15A and 15B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 13. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 16A, 16B:
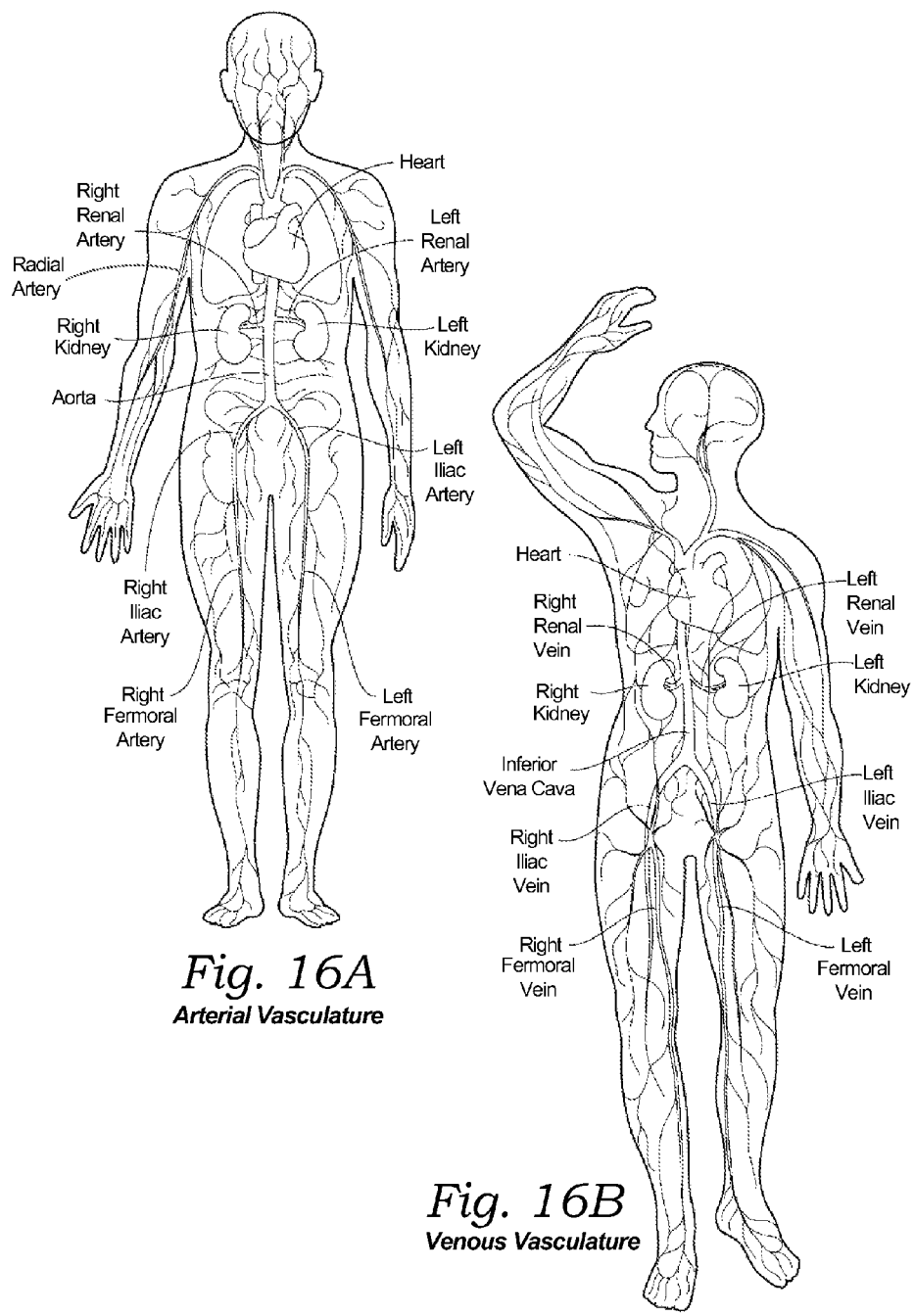
FIGS. 16A and 16B show the arterial vascular system and venous system of the human body, respectively.

In accordance with the present technology, neuromodulation of a left and/or right renal plexus RP, which is intimately associated with a left and/or right renal artery, may be achieved through intravascular access. As FIG. 16A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 16B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of catheter, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Catheter, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory catheter and a luminal surface or wall of a renal artery. When the neuromodulatory catheter includes an energy delivery element (e.g., electrode regions), consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory catheter and a luminal surface of the artery, nerves in and around the adventia of the artery should be safely modulated via the neuromodulatory catheter. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory catheter should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory catheter to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory catheter may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment catheter to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the catheter, systems and methods utilized to achieve renal neuromodulation, such properties of the renal arteries, also may guide and/or constrain design characteristics.

As noted above, a catheter positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 10 cm (4 inches) cranially with respiratory excursion. This may impart significant motion to the renal artery connecting the aorta and the kidney, thereby requiring from the neuromodulatory catheter a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

IV. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively. It will also be appreciated that various modifications may be made without deviating from the technology. For example, an intraluminal energy delivery device in accordance with the technology may comprise two or more strut-type electrode arrays and no finger-type electrode array, and other combinations of types of electrode arrays are considered to be within the technology.

We claim:

1. A catheter comprising:
   a control rod including an electrical conductor; and
   an intraluminal energy delivery device disposed at a distal end of the control rod and electrically coupled to the conductor, the energy delivery device including:
      a first metal electrode array comprising a plurality of flexible elongate struts extending from a proximal strut junction to a distal strut junction;
      wherein the first array has a tendency to transform from a radially constrained elongate configuration to a preformed radially expanded basket configuration;
      wherein, in the basket configuration, each of the plurality of struts has a main body that is bowed radially outwardly to form a peak between the first proximal strut junction and the distal strut junction; and
      wherein each strut peak defines an electrode region configured, when the first array is in the basket configuration, to deliver therapeutically-effective energy to tissue at a first treatment site within a blood vessel of a human patient;
      a second metal electrode array comprising a plurality of flexible elongate fingers extending distally from a finger junction;
      wherein the second array has a tendency to transform from a radially constrained elongate configuration to a preformed splayed configuration;
      wherein each of the plurality of fingers has a distal tip portion defining an electrode region configured, when the second array is in the splayed configuration, to deliver therapeutically-effective energy to tissue at a second treatment site within the blood vessel of the human patient; and
      a first metal connection portion flexibly joining the distal strut junction and the finger junction,
   wherein the intraluminal energy delivery device is formed from a single thin-walled metal tube without any joints.

2. The catheter of claim 1 wherein the intraluminal energy delivery device further comprises:
   a tubular metal retainer portion adapted to fixedly receive the distal end of the control rod; and
   a second metal connection portion flexibly joining the retainer portion and the proximal strut junction.

3. The catheter of claim 2 wherein each of the retainer portion, the proximal and distal strut junctions and the finger junction has a thin-walled tubular metal body, and wherein any or all of the retainer portion, the proximal and distal strut junctions and the finger junction has one or more longitudinal slots to provide reduced longitudinal bending stiffness as compared to an unslotted thin-walled tubular metal body of the same dimensions.

4. The catheter of claim 1 wherein the plurality of struts comprises only three struts spaced substantially equally about a longitudinal axis of the energy delivery device.

5. The catheter of claim 4 wherein the plurality of fingers comprises only three fingers spaced substantially equally about the longitudinal axis of the energy delivery device and circumferentially offset from the only three struts at an angle of between 0 and about 60 degrees.

6. The catheter of claim 1 wherein the energy delivery device is formed integrally at a distal portion of the control rod without any joints.

7. The catheter of claim 1 wherein the control rod is made of an electrically conductive material to form the conductor.

8. The catheter of claim 1 further comprising an elongate hollow shaft adapted to slidably receive and constrain the intraluminal energy delivery device with the first and second arrays in their respective radially constrained elongate configurations.

9. The catheter of claim 1 wherein, when the first array is in the expanded configuration and the second array is in the splayed configuration, the intraluminal energy delivery device includes a central region having a substantially hourglass shape, and wherein the central region includes the connection portion and adjacent portions of the first and second arrays.

10. The catheter of claim 1 wherein the connection portion includes at least one articulation feature configured to permit substantial angular misalignment between the first and second arrays using negligible bending forces.

11. The catheter of claim 10 wherein the at least one articulation feature includes a helical configuration.

12. The catheter of claim 1 wherein one or more of the plurality of flexible elongate struts and/or one or more of the plurality of fingers comprises a pair of parallel spaced-apart arms.

13. The catheter of claim 1 further comprising an energy source electrically coupled to the conductor, wherein the first and second electrode arrays are configured to deliver energy from the energy source to the tissue at the treatment site.

14. The catheter of claim 1 wherein, when the first array is in the expanded configuration and the second array is in the splayed configuration, the struts of the first array define closed cells therebetween, and the struts of the second array define open cells therebetween.

15. A method of delivering energy to a human patient, the method comprising:
  expanding a first electrode array of an intraluminal energy delivery device to radially move at least one first electrode region of the first array into contact with a wall of a blood vessel of the patient, wherein the intraluminal energy delivery device is formed from a single thin-walled metal tube without any joints;
  expanding a second electrode array of the intraluminal energy delivery device to radially move at least one second electrode region of the second array into contact with the wall of the blood vessel of the patient, the second array being disposed distally of the first array; and
  delivering energy to the wall of the blood vessel via the at least one first electrode region and the at least one second electrode region while substantially all of a portion of the intraluminal energy delivery device located between the first array and the second array is spaced-apart from the wall of the blood vessel.

16. The method of claim 15 further comprising allowing fluid in a lumen of the blood vessel to flow through the first and second arrays while delivering the energy to the wall of the blood vessel.

17. The method of claim 16, further comprising:
  navigating the intraluminal energy delivery device into the lumen of the blood vessel; and
  releasing the first and second arrays to self-expand to radially move the respective electrode regions into contact with the wall of the blood vessel.

* * * * *